(12) United States Patent
Cook

(10) Patent No.: US 7,784,464 B2
(45) Date of Patent: *Aug. 31, 2010

(54) LARYNGEAL MASK

(75) Inventor: Daniel J. Cook, St. Louis, MO (US)

(73) Assignee: Cookgas, LLC, St. Louis, MO (US)

( * ) Notice: Subject to any disclaimer, the term of this patent is extended or adjusted under 35 U.S.C. 154(b) by 818 days.

This patent is subject to a terminal disclaimer.

(21) Appl. No.: 11/532,281

(22) Filed: Sep. 15, 2006

(65) Prior Publication Data

US 2008/0066762 A1    Mar. 20, 2008

(51) Int. Cl.
*A61M 16/00* (2006.01)
*A62B 9/06* (2006.01)

(52) U.S. Cl. .............. 128/207.14; 128/207.15
(58) Field of Classification Search ............ 128/207.14, 128/207.15, 206.21, 200.26, 206.29
See application file for complete search history.

(56) References Cited

U.S. PATENT DOCUMENTS

| | | |
|---|---|---|
| 678,814 A | 7/1901 | Riggs |
| 1,345,425 A | 7/1920 | Wells |
| 2,335,741 A | 11/1943 | Contaldi |
| 2,787,010 A | 4/1957 | Uphoff |
| 3,139,088 A | 6/1964 | Galleher, Jr. |
| 3,434,100 A | 3/1969 | Dykzeul |
| 3,606,669 A | 9/1971 | Kemble |
| 3,734,100 A | 5/1973 | Walker et al. |
| 3,756,601 A | 9/1973 | Frey et al. |
| 3,945,069 A | 3/1976 | Cecil |
| 4,146,034 A | 3/1979 | Gupta |
| 4,231,365 A | 11/1980 | Scarberry |
| 4,327,720 A | 5/1982 | Bronson et al. |
| 4,340,046 A | 7/1982 | Cox |
| 4,388,076 A | 6/1983 | Waters |
| 4,444,201 A | 4/1984 | Itoh |
| 4,509,512 A | 4/1985 | LeClercq |
| 4,509,514 A | 4/1985 | Brain |
| 4,520,810 A | 6/1985 | Weiss |
| RE31,948 E | 7/1985 | Deutsch et al. |
| 4,540,959 A | 9/1985 | Saad |
| 4,582,056 A | 4/1986 | McCorkle, Jr. |
| 4,593,687 A | 6/1986 | Gray |
| 4,661,028 A | 4/1987 | Sanger |
| 4,674,496 A | 6/1987 | Svadijan et al. |
| 4,751,922 A | 6/1988 | DiPietropolo |
| 4,791,923 A | 12/1988 | Shapiro |
| 4,825,861 A | 5/1989 | Koss |

(Continued)

OTHER PUBLICATIONS

"Products—LMA Fastrach," http://www.lmana.com/prod/components/products/lma_fastrach.html, printed on Jun. 19, 2005, one page.

(Continued)

*Primary Examiner*—Steven O Douglas
*Assistant Examiner*—Colin Stuart
(74) *Attorney, Agent, or Firm*—Lewis, Rice & Fingersh, L.C.

(57) ABSTRACT

A supraglottic airway of the type used to facilitate lung ventilation and the insertion of endo-tracheal tubes or related medical instruments through a patient's laryngeal opening where the shield is constructed of a generally single-use blow-molded structure.

5 Claims, 5 Drawing Sheets

U.S. PATENT DOCUMENTS

| | | | |
|---|---|---|---|
| 4,863,439 A | 9/1989 | Sanderson | |
| 4,872,483 A | 10/1989 | Shah | |
| 4,895,533 A | 1/1990 | Yagi | |
| 4,919,127 A | 4/1990 | Pell | |
| 4,995,388 A | 2/1991 | Brain | |
| 5,024,220 A | 6/1991 | Holmgreen et al. | |
| 5,033,919 A | 7/1991 | Choe | |
| 5,037,251 A | 8/1991 | Roth | |
| 5,042,475 A | 8/1991 | LaBombard | |
| 5,071,413 A | 12/1991 | Utterberg | |
| 5,197,463 A | 3/1993 | Jeshuran | |
| 5,218,970 A | 6/1993 | Turnbull et al. | |
| 5,222,487 A | 6/1993 | Carr et al. | |
| 5,253,658 A | 10/1993 | King | |
| 5,277,178 A | 1/1994 | Dingley | |
| 5,279,610 A | 1/1994 | Park et al. | |
| 5,282,464 A | 2/1994 | Brain | |
| 5,303,697 A | 4/1994 | Brain | |
| 5,324,080 A | 6/1994 | McNaughton et al. | |
| 5,326,196 A | 7/1994 | Noll | |
| 5,340,165 A | 8/1994 | Sheppard | |
| 5,355,879 A | 10/1994 | Brain | |
| 5,391,248 A | 2/1995 | Brain | |
| 5,392,774 A | 2/1995 | Sato | |
| 5,393,101 A | 2/1995 | Matkovich | |
| 5,477,852 A | 12/1995 | Landis et al. | |
| 5,509,408 A | 4/1996 | Kurtis | |
| 5,513,627 A | 5/1996 | Flam | |
| 5,527,316 A | 6/1996 | Stone | |
| 5,529,582 A | 6/1996 | Fukuhara | |
| 5,545,048 A | 8/1996 | Maeda | |
| 5,546,937 A | 8/1996 | Stuart et al. | |
| 5,562,371 A | 10/1996 | Reed | |
| 5,562,673 A | 10/1996 | Koblish et al. | |
| 5,569,222 A | 10/1996 | Haselhorst et al. | |
| 5,579,762 A | 12/1996 | Lee | |
| 5,584,290 A | 12/1996 | Brain | |
| 5,588,424 A | 12/1996 | Insler et al. | |
| 5,590,643 A | 1/1997 | Flam | |
| 5,623,921 A | 4/1997 | Kinsinger et al. | |
| 5,632,271 A | 5/1997 | Brain | |
| 5,643,174 A | 7/1997 | Yamamoto et al. | |
| 5,653,231 A | 8/1997 | Bell | |
| 5,655,519 A | 8/1997 | Alfery | |
| 5,682,880 A | 11/1997 | Brain | |
| 5,711,296 A | 1/1998 | Kolobow | |
| 5,713,348 A | 2/1998 | Pell | |
| 5,720,749 A | 2/1998 | Rupp | |
| 5,743,258 A | 4/1998 | Sato | |
| 5,772,643 A | 6/1998 | Howell et al. | |
| 5,787,879 A | 8/1998 | Gibson | |
| 5,878,745 A | 3/1999 | Brain | |
| 5,881,726 A | 3/1999 | Neame | |
| 5,896,858 A | 4/1999 | Brain | |
| 5,937,860 A | 8/1999 | Cook | |
| 5,947,120 A | 9/1999 | Bailey | |
| 5,961,489 A | 10/1999 | Hirota | |
| 5,979,445 A | 11/1999 | Neame et al. | |
| 6,021,779 A | 2/2000 | Pagan | |
| 6,050,264 A * | 4/2000 | Greenfield | 128/207.15 |
| 6,196,224 B1 | 3/2001 | Alfery | |
| 6,240,922 B1 | 6/2001 | Pagan | |
| 6,261,401 B1 | 7/2001 | Pagan | |
| 6,374,827 B1 | 4/2002 | Bowden et al. | |
| 6,386,199 B1 | 5/2002 | Alfery | |
| 6,422,239 B1 | 7/2002 | Cook | |
| 6,450,164 B1 | 9/2002 | Banner et al. | |
| 6,612,305 B2 | 9/2003 | Fauza | |
| 6,631,720 B1 | 10/2003 | Brain | |
| 6,668,821 B2 | 12/2003 | Christopher | |
| 6,705,318 B1 | 3/2004 | Brain | |
| 6,705,320 B1 | 3/2004 | Anderson | |
| 6,705,321 B2 | 3/2004 | Cook | |
| 6,705,322 B2 | 3/2004 | Chang | |
| 6,729,325 B2 | 5/2004 | Alfery | |
| 6,892,731 B2 | 5/2005 | Cook | |
| 6,899,147 B2 | 5/2005 | Ogawa et al. | |
| 6,923,176 B2 | 8/2005 | Ranzinger | |
| 6,935,153 B2 | 8/2005 | Frigo et al. | |
| 6,983,744 B2 | 1/2006 | Alfery | |
| 7,013,899 B2 | 3/2006 | Alfery | |
| 7,021,686 B2 | 4/2006 | Glasgow et al. | |
| 7,040,312 B2 | 5/2006 | Alfery et al. | |
| 7,040,322 B2 | 5/2006 | Fortuna | |
| 7,089,943 B2 * | 8/2006 | Chang | 128/207.15 |
| 7,096,868 B2 | 8/2006 | Tateo et al. | |
| 7,097,802 B2 | 8/2006 | Brain | |
| 7,128,071 B2 | 10/2006 | Brain | |
| 2001/0025641 A1 * | 10/2001 | Doane et al. | 128/207.15 |
| 2001/0050082 A1 | 12/2001 | Christopher | |
| 2003/0037790 A1 * | 2/2003 | Brain | 128/207.14 |
| 2004/0020491 A1 | 2/2004 | Fortuna | |
| 2004/0079364 A1 | 4/2004 | Christopher | |
| 2005/0016529 A1 | 1/2005 | Cook | |
| 2005/0051173 A1 | 3/2005 | Brain | |
| 2005/0139220 A1 | 6/2005 | Christopher | |
| 2006/0027238 A1 | 2/2006 | Lin | |
| 2006/0076021 A1 | 4/2006 | Chang | |
| 2006/0180156 A1 | 8/2006 | Baska | |
| 2006/0207597 A1 | 9/2006 | Wright | |
| 2007/0028923 A1 | 2/2007 | Souris et al. | |
| 2007/0102001 A1 | 5/2007 | Brain | |
| 2007/0137651 A1 | 6/2007 | Glassenberg et al. | |
| 2007/0246050 A1 | 10/2007 | Parikh et al. | |
| 2008/0078398 A1 | 4/2008 | Cook | |

OTHER PUBLICATIONS

"9c Removal of LMA-Fastrach Prior to Extubation," LMA-Fastrach Instructional Manual, www.lmana.com/docs/fastrach_instruction.pdf, Feb. 2002, pages cover (2 pages), 26-27.

Byrd, Jr., R.P."Ventilation, Mechanical," http://www.emedicine.com/med/topic3370.htm, Jul. 6, 2006, pp. 1-13.

"Ambu Product Information," Ambu A/S, 2007, pp. 1-18, Denmark.

"Intersurgical Complete Respiratory Systems," http://www.intersurgical.com/productscatalog/choosegroup.aspx?cm..., printed on Apr. 11, 2007, one page.

"LMA Airway Instruction Manual," The Laryngeal Mask Company Limited, www.lmana.com/docs/LMA_Airways_Manual.pdf, 2005, pp. 1-23.

International Search Report, International Patent Application No. PCT/US2008/060425, mailed Sep. 29, 2008, 11 pages.

* cited by examiner

LARYNGEAL MASK

BACKGROUND

1. Field of the Invention

The invention relates to an artificial airway device, more specifically to a supraglottic airway designed to be easily manufactured and preferably single use.

2. Description of the Related Art

In general, supraglottic airways such as laryngeal masks allowing for both rapid lung ventilation and the insertion of medical instruments and tubes into the laryngeal openings of patients have been described in patents, such as U.S. Pat. No. 4,509,514 to Brain and U.S. Pat. Nos. 6,422,239 and 5,937,860 to Cook the entire disclosures of which were herein incorporated by reference. Laryngeal masks generally consist of two major components, a breathing tube and an inflatable shield, these devices are inserted into a patient's throat, and when properly positioned, cover the laryngeal opening. A seal is then formed around the circumference of the laryngeal opening by the inflation of a ring-like structure located toward the front of the mask (patient end). Inflation of the ring exerts pressure against the front, sides, and rear portions of the oropharynx, securing the device in place such that the laryngeal opening is positioned in alignment with a recessed cavity in the mask face. Extending from a point external to the oral cavity, the flexible breathing tube terminates within the recessed cavity, aligned axially with the laryngeal opening. The positioning of the flexible breathing tube allows the passage of endo-tracheal tubes or related medical instruments into the laryngeal opening, in addition to allowing for lung ventilation.

While current supraglottic airways such as laryngeal masks can provide for improved placement and breathing over a traditional endotracheal tube, they can still be improved. In particular, many laryngeal masks are constructed through relatively expensive and complex construction techniques. This can result in a fairly expensive device that requires repeated sterilization and reuse to be cost effective. As hospitals and other care centers become increasingly cost conscious and focused on efficiency, it is desirable to provide devices which are always immediately available for use and which eliminate the need for sterilization costs.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein is a supraglottic airway primarily intended to facilitate lung ventilation and the insertion of endo-tracheal tubes or related medical instruments into a patient's trachea as needed during general anesthesia, intensive care, critical patient care, or at any other time that ventilation would be desired. In a laryngeal mask embodiment of such a supraglottic airway, the mask comprises a flexible ventilation tube and an inflatable positioning shield generally conforming to the anatomy of the oropharynx region surrounding the laryngeal opening, and securely affixed to the distal end of the ventilation tube. The shield is preferably constructed of a single piece such as utilizing blow-molding techniques. The tube is then attached thereto along with the inflation pump to provide for a device of relatively simple assembly.

Described herein, among other things, is a laryngeal mask airway comprising; a respiratory tube having a distal end, a proximal end, and a length therebetween; a shield comprising an inflatable outer ring and a posterior base wherein the shield is formed as a single hollow balloon having an entry point at a proximal end, the shield having two opposing surfaces of the hollow balloon pushed together and attached to form the posterior base, the remaining structure encircling the posterior base forming the outer ring, the posterior base being the base of a recessed cavity and the outer ring surrounding the recessed cavity; and an inflation tube having a distal end, a proximal end, and a length therebetween; wherein, a hole is cut into the outer ring in an area adjacent the posterior base; wherein the respiratory tube is threaded through the hole and the entry point so that the distal end of the respiratory tube is placed adjacent the posterior base in the recessed cavity; wherein a distal end of the inflation tube is placed within the outer ring; and wherein the shield, the respiratory tube, and the inflation tube are adhered together so that air can pass from the inflation tube into the outer ring, which is otherwise sealed, and air can pass through the respiratory tube from the proximal end, to the distal end, but is otherwise sealed.

In an embodiment of the airway the respiratory tube is smoothly curved. The respiratory tube may also include a wedge section comprising a wedge, a groove, and a raised disk wherein the wedge is positioned within the recessed cavity when the shield, the respiratory tube, and the inflation tube are adhered together.

In an embodiment of the airway the shield is formed by blow-molding and may include a connection nozzle on the proximal end, which is removed and discarded prior to the threading.

In an embodiment, the airway also includes a connector removeably attached to the proximal end of the respiratory tube and may be designed for disposal after a single-use.

There is also described herein, a method of constructing a laryngeal mask airway; the method comprising providing a respiratory tube having a distal and a proximal end; blow-molding a shield, the shield comprising an inflatable outer ring formed of a single layer of material and a posterior base formed of at least a double layer of material; providing an inflation tube having a distal and a proximal end; assembling the airway by inserting the respiratory tube through the outer ring in such a manner that the respiratory tube intersects the outer ring so that a portion of the respiratory tube seals off a portion of the outer ring; and placing the distal end of the inflation tube within the outer ring.

In an embodiment the posterior base is the base of a recessed cavity surrounded by the outer ring and the distal end of the respiratory tube extends into the recessed cavity.

In an embodiment, the double layer of the posterior base is at least twice as thick of the single layer of the inflatable outer ring and the airway may be intended to be disposed of after a single use.

DESCRIPTION OF THE PREFERRED EMBODIMENT(S)

The following detailed description illustrates by way of example and not by way of limitation. Described herein, among other things, is an embodiment of a supraglottic airway which is designed to be simpler to construct than prior designs and can be suitable for a single-use disposable device. Specifically, the supraglottic airway has a shield (201) constructed as a single structure, generally which is blow-molded, to allow for improved ease of assembly and speed of manufacture. While the supraglottic airway described herein incorporates certain features in the shape and features of the shield (201) for improved placement in the airway, it should be recognized that these features are not required and the techniques of manufacture can be used on airways of other shapes and forms.

Figure 1:
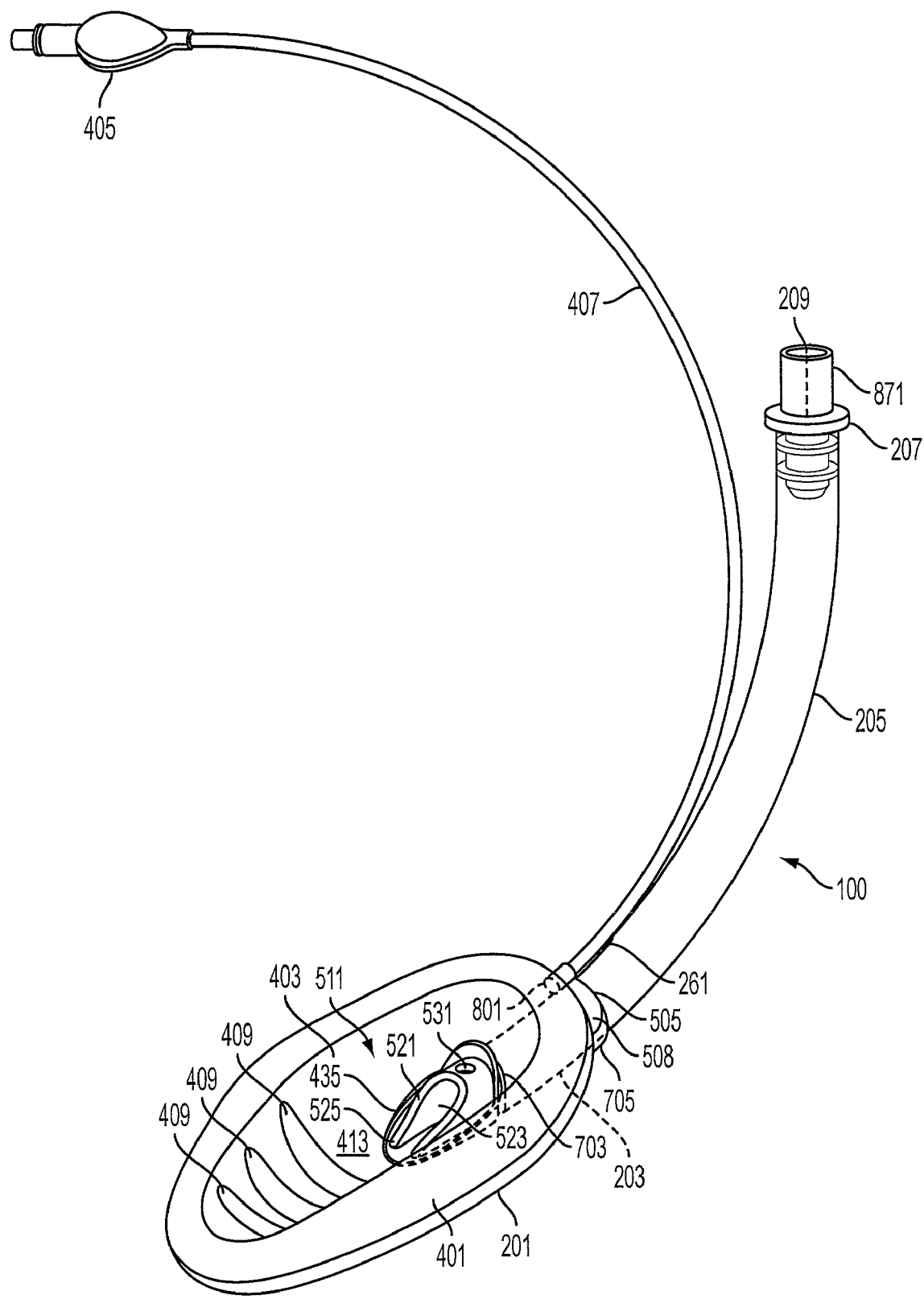
FIG. 1 shows a perspective view of an embodiment of a laryngeal mask as assembled.

FIG. 1 provides for an embodiment of a supraglottic airway in the form of removable laryngeal mask airway (100). This mask (100) is chosen as an exemplary form of supraglottic airway to simply demonstrate how the systems and methods of construction and assembly discussed herein can be used. It is in no way intended to be descriptive of all airways which may be used in other embodiments. In the depicted embodiment, the laryngeal mask (100) generally comprises three major components. There is an inflatable positioning shield (201) which is secured toward the distal end (203) of a respiratory tube (205) formed into an arcuate curve. There is also an inflation pump (405) and inflation tube (407) designed to provide for inflation and deflation of at least a portion of the shield (201). The laryngeal mask (100) is generally composed of a relatively soft flexible material such as, but not limited to, silicone-rubber polymer or plastics.

The inflatable positioning shield (201) comprises a generally wedge-shaped ellipsoid, ovoid, or toroid outer ring (401) with a pliable molded posterior base (403) attached thereto so that the posterior base (403) forms the base of, and the outer ring (401) surrounds, a recessed cavity (511). The outer ring (401) is preferably repeatedly inflatable and deflatable with such inflation being accomplished by attachment of an inflation device or pump (405) which is capable of pulling air from the ambient, into an inflation tube (407) and from there into the interior of the outer ring (401). The outer ring (401), when inflated, is sized and shaped to generally conform to the approximate available space in the oropharynx region.

The posterior base (403) is secured longitudinally within the hole in the center of the outer ring (401). The posterior base (403) is generally attached in a fashion to form an elongated and tapered hemisphere relative the generally major plane of the outer ring (401) so as to give the shield (201) an overall shape such as that seen in the FIGS. In the depicted embodiment, there are semi-rigid raised ridges (409) positioned longitudinally parallel to each other along the surface (413) of the posterior base (403) "inside" the hole of the outer ring (401).

Figure 3:
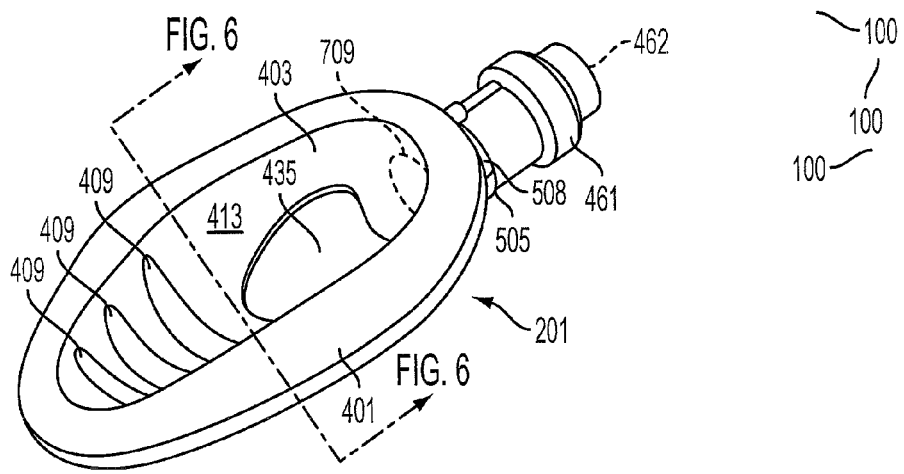
FIG. 3 shows a perspective view of a shield that has been blow-molded and not yet trimmed.

The shield (201), in a preferred embodiment, is constructed from a single blow-molded construction which is formed into the outer ring (401) and posterior base (403) by blowing the structure into a shaped die. As can be seen in FIG. 3, the shield when originally blow-molded accompanies a single hollow structure or "balloon." The shield (201) is formed as it appears in FIG. 1 but further includes a connection nozzle (461) attached to the proximal end (505). The connection nozzle (461) is the original source of material for the blow-molding and will be removed and discarded, however it serves to initially define an entry point (462) to the interior of the balloon which will be used to form the shield (201).

Figure 6:
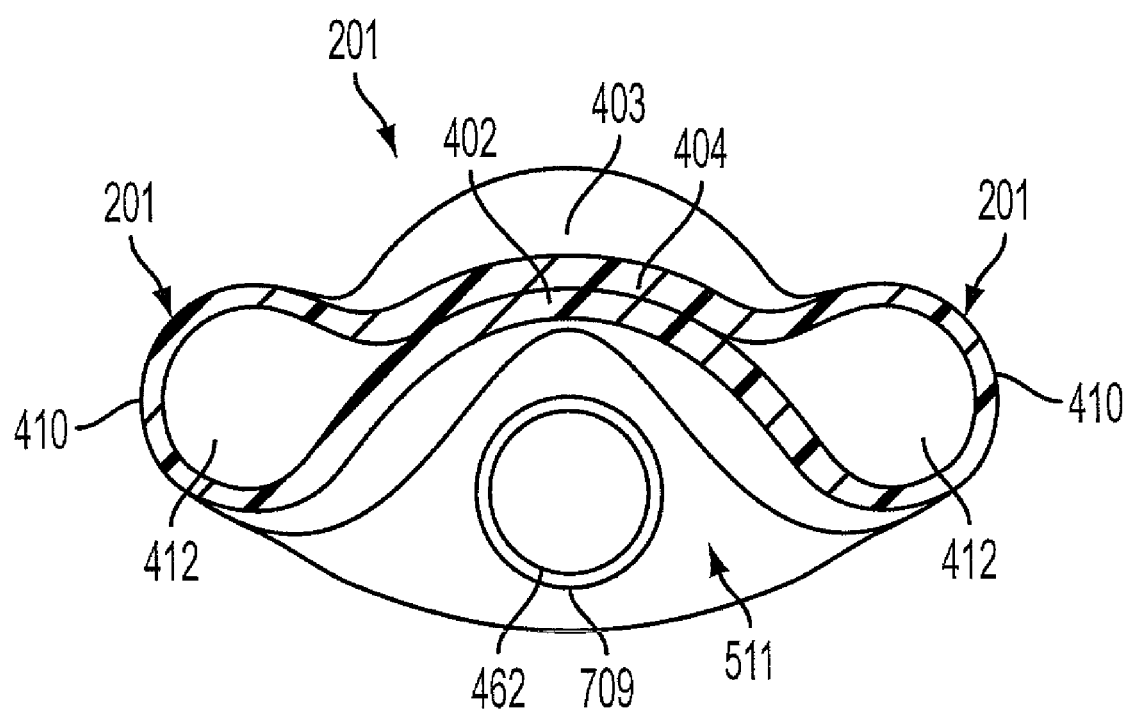
FIG. 6 shows a cut-through along line 6-6 in FIG. 3.

Blow-molding techniques generally require that the structure to be formed comprise a hollow balloon which is then pushed or molded into shape. FIG. 3 shows the appearance of the outer surface of the balloon when molded into a shield (201). FIG. 6 shows a cross-section of the shield of FIG. 3 indicating how the shield (201) is preferably constructed to indicate how the balloon is compressed and formed into the desired structure shown in FIG. 3. As can be seen in FIG. 6, the outer ring (401) and posterior base (403) are formed by taking the opposing sides of the balloon and partially pushing them together at an interior location so that they touch at a point spaced from the entry point (462) and the neck (508). These opposing sides are then adhered together either through the use of an adhesive or simply through the adhesive capabilities of the material being formed so as to form the posterior base (403) and outer ring (401) as shown in the FIGS. As should be apparent, this style of formation results in a structure whereby the outer ring (401) forms a generally toroidal structure as discussed previously including a hollow (412) and the posterior base (403) does not allow for air passage between the two surfaces which form its upper (402) and lower (404) portions thereby forming a generally solid base attached to the outer ring (401) and resulting in the "dish" shape of FIG. 3.

As can be further seen in FIG. 6, the posterior base (403) is thicker than either of the outer surfaces (410) of the outer ring (401) which provides additional strength to the shield (201) as a whole. At the same time, however, the structure is not rigid and is capable of bending during insertion. In a preferred embodiment, the outer surfaces (410) are in fact molded to be significantly thinner than each of the upper portion (402) and lower portion (404) to provide for even more strength to the posterior base (403).

The shield (201) is generally connected to the respiratory tube (205) by means of a hollow wedge (501) which allows the respiratory tube (205) to pass through the shield (201) and into the recessed cavity (511) formed above the posterior base (403) and inside the "hole" of the outer ring (401). In a preferred assembly, the hollow wedge (501) is attached generally to the distal end (203) of the respiratory tube (205) as is visible in FIG. 4 and comprises a somewhat more rigid construction than the other components. The wedge section may be inserted into the end of the respiratory tube, or may be co-molded in an alternative embodiment. The wedge section preferably includes the wedge (501) as well as a groove (551) which is circumferentially arranged toward the distal end (203) of the respiratory tube (205) and a raised disk (553) placed distal of the groove (551) but proximal the wedge (501).

The respiratory tube (205) passes through a first airtight peripheral seal (703) to exit the recessed cavity (511) and a second airtight peripheral seal (705) towards the proximal end (505) of the inflatable positioning shield (201). The wedge (501) therefore gives an access into the shield recess (511) from the interior of the respiratory tube (205) allowing air to pass from the recessed cavity (511) into the distal end (203) of the respiratory tube (205) and from there out the proximal end (207) of the respiratory tube (205) without passing into the outer ring (401). The wedge (501) is generally formed into an angle (521) to the length of the respiratory tube (205) which is generally between 0 and 90 degrees and preferably about 30 to about 35 degrees with the posterior base (403), forming an elongated elliptically shaped distal lumen (523) open to the interior of the shield recess (511) and interior of the respiratory tube (205).

There may also be included a ventilation lumen (531) through the wedge (501) to provide an alternate airway in the event the distal lumen (523) becomes obstructed during patient lung ventilation. The ventilation lumen (531) also generally prevents the formation of a pressure differential between the recessed cavity (511) and flexible respiratory tube (205). Absent a pressure differential, any object obstructing the distal lumen (523) will not generally become inextricably lodged.

The respiratory tube (205) may be formed in any manner known to those of ordinary skill in the art but will generally form a smoothly curving hollow cylinder of generally circular or elliptical cross-section preferably approximating, for ease of insertion, the shape of the human throat. The respiratory tube (205) is preferably sized and shaped to accommodate the passage of endo-tracheal tubes and related medical devices up to 8.5 French in diameter. The length of respiratory tube (205) is such that when the laryngeal mask (100) is properly positioned for use within the oropharynx, the attachment (proximal) end (207) of respiratory tube (205) is located exterior to the oral cavity of the patient. The attachment end (207) of the respiratory tube (205) terminates in an unobstructed proximal lumen (209), providing a direct pathway through the respiratory tube (205) to the distal end (203) and distal lumen (523). In alternative embodiments, the attachment end (207) may be fitted with removable adapters or connectors (871) suitable for connection to a variety of medical devices, for example, lung ventilation machines.

There is also included on the respiratory tube (205) a grooved recess (261) which is placed on the inside curve of the respiratory tube (205). This grooved recess (261) allows for the inflation tube (407) to be placed in more defined contact with the respiratory tube (205) and also be connected to the shield (201) via the second airtight seal (705). As shown in FIG. 1, the inflation tube (407) will generally be adhered to the respiratory tube (205) at the groove (261) and will extend along the respiratory tube (205) a predetermined distance through the second seal (705).

Figure 2:
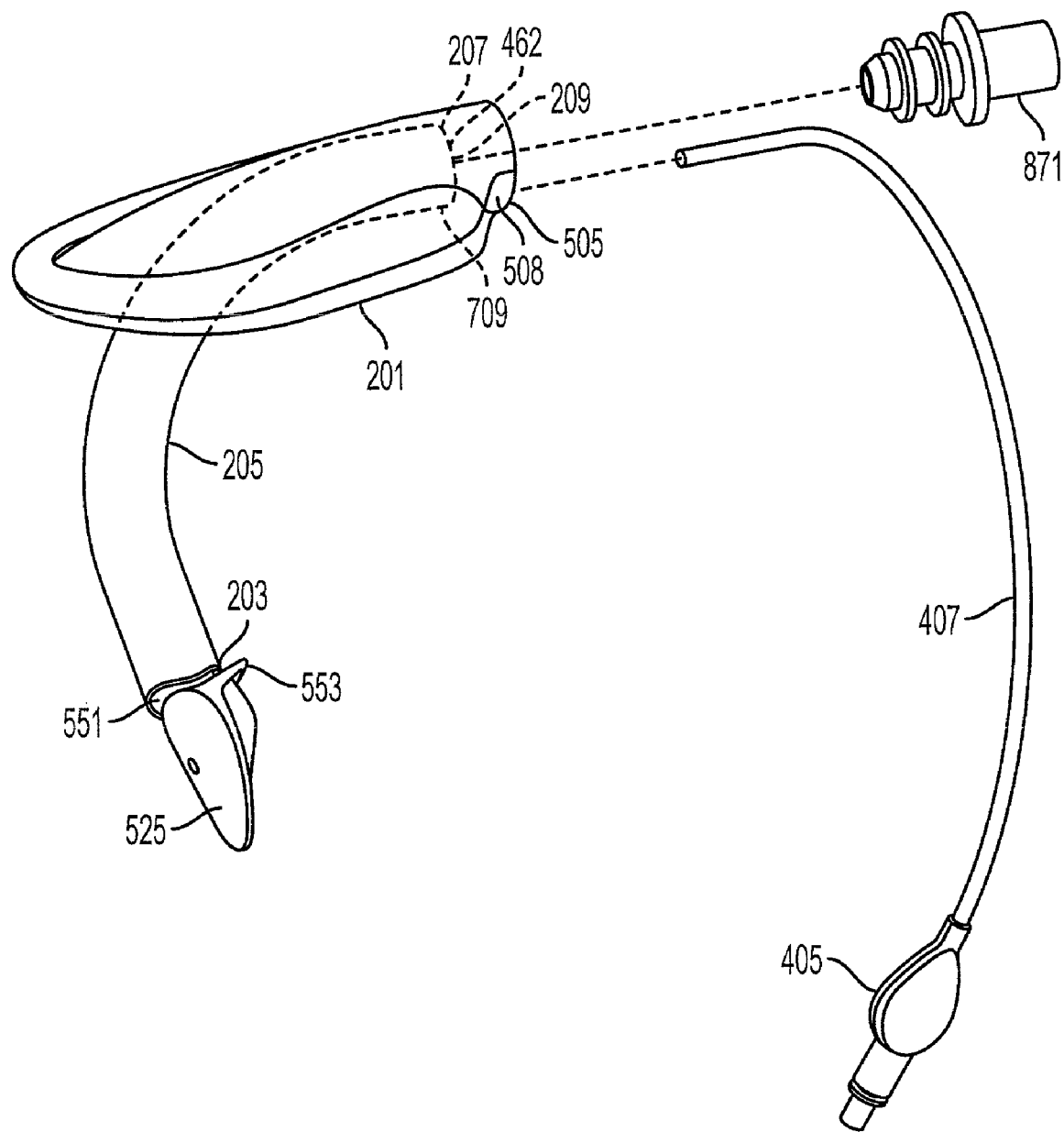
FIG. 2 shows a partially exploded view of the embodiment of FIG. 1 to show the manner of assembly.
Figure 4:
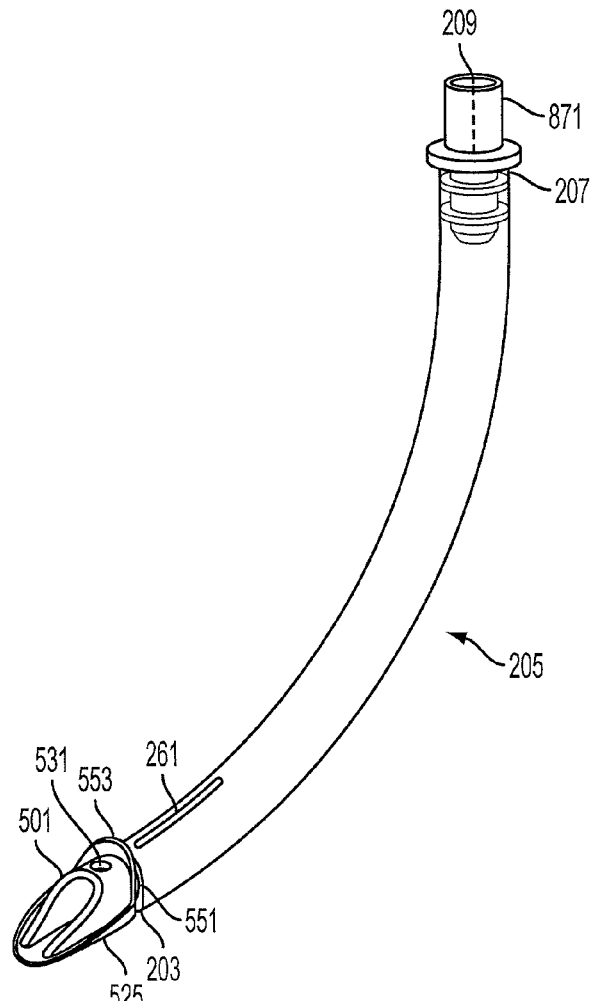
FIG. 4 shows a perspective view of a breathing tube.
Figure 5:
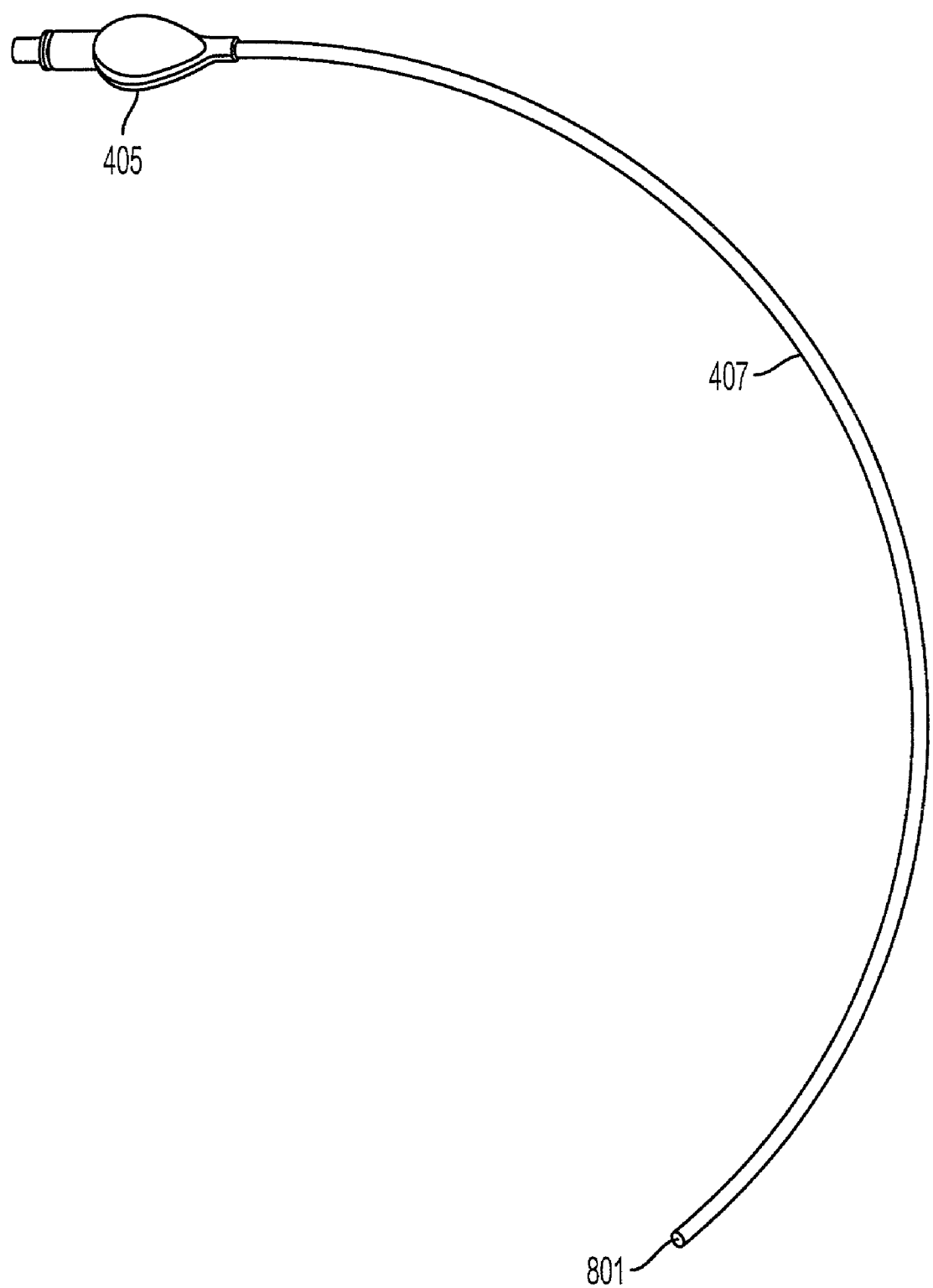
FIG. 5 shows a perspective view of an inflation pump and tube.

In order to assemble the mask (100), it is generally preferred that the following steps be performed to assemble the components, generally as indicated in FIG. 2. First the components are formed as shown in FIGS. 3-5. The shield (201) then has a hole (709) cut through the proximal wall of the recess (511) as shown in FIG. 6 and the connection nozzle (461) is removed. As should be apparent from FIGS. 3 and 6, the entry point (462) and hole (709) therefore present a relatively straight passage which extends from inside the recess (511) through the outer ring (401) and out the proximal end (505). There is also generally formed a connection recess (435) in the posterior base (403). This may be cut out or may be formed by simple compression of the material forming the posterior base (403).

The respiratory tube (205) is now inserted, proximal end (207) first, through the hole (709), passed through the outer ring (401), and extended out the entry point (462) and thus the posterior end (505) of the shield (201). The hole (709) and entry point (462) are preferably sized and shaped to be of relatively similar size to the exterior diameter of the respiratory tube (205) so that a tight connection is formed by the respiratory tube (205) distending the material of the shield (201) slightly in both places. The respiratory tube (205) will continue to be slid through the hole (709) and entry point (462) until the hole (709) interacts with the groove (551) and disk (553). At that point, the wedge (501) and disk (553) will generally be the only portions of the respiratory tube (205) which has not passed through the hole (709) and the reinforced support (525) will be adjacent to the recess (435) in the posterior base (403). These pieces will then be connected together resulting in the wedge (501) being positioned in the recess (511) and generally flush with the interior of the posterior base (403). The connection between the posterior base (403) and the reinforced support (525) may be formed in any manner known to one of ordinary skill in the art, however, in a preferred embodiment, the two devices are adhered together with a generally non-separable adhesive. The respiratory tube (205) now is arranged to generally pass through the outer ring (401) in such a fashion as to form a first airtight seal (703) and a second airtight seal (705) which inhibit air in the outer ring (401) from entering the respiratory tube (205) and vice-versa.

In the depicted embodiment, the disk (553) and groove (551) formed toward the distal end (203) of the respiratory tube (205) serve to further reinforce the first airtight seal (703). In particular, the material surrounding the hole (709) will end up being stretched by the passing of the respiratory tube (205) until the hole (709) is aligned with the groove (551). The material will then relax and the hole (709) will collapse slightly into the groove (551). This provides a first level of sealing. The disk (553) adjacent to the hole (709) can then be provided with an adhesive which adheres to the shield (201) forming the airtight seal (703).

At the proximal end (505) of the shield (201), once the respiratory tube (205) is in position, the distal end (801) of the inflation tube (407) can be positioned to extend through the recessed groove (261) so that the distal end (801) is placed into the outer ring (401). The proximal end (505) of the shield (201) is then also provided with an adhesive in the neck (508) to form a second airtight seal between all of the respiratory tube (205), the inflation tube (407), and the proximal end (505) of the shield (201).

As should be apparent, once assembled the two airtight seals (703) and (705) serve to isolate the interior of the outer ring (401) from the interior of the respiratory tube (205). There is preferably no air transmission between these two devices. Further, as the distal end (801) of the inflation tube (407) is within the outer ring (401), and also sealed from the respiratory tube (205) and the outside air, the pump (405) can be used to provide or remove air into the outer ring (401). This results in its inflation or deflation as desired. The respiratory tube (205) provides for an opening from within the recessed cavity (511) of the shield (201), through the interior of the respiratory tube (205). This allows for a patient to breath through the respiratory tube (205) once it is in position. The removable connector (801) may also then be attached to the proximal end (207) of the respiratory tube (205) if desired.

While in the above embodiment as depicted in FIG. 2, the proximal end (207) of the respiratory tube is first threaded through the hole (703) and entry point (462), in an alternative embodiment, the wedge (501) and respiratory tube (403) may actually be inserted in the opposing direction to the embodiment shown in FIG. 2. In this alternative embodiment, the wedge section and the distal end (203) of the respiratory tube (205) would be first inserted through the entry point (462), run through the outer ring (401), and exit the hole (703). While this method is viable in most cases, it is generally not preferred as it is usually more difficult to perform. Further, in some embodiments, it may require redesign of the wedge section components (such as the wedge (501), disk (553), or reinforced support (525) to prevent damage to the hole (703) and entry point (462) during the wedge passing through those structures.

Generally, use of the laryngeal mask (100) would proceed as follows. Before insertion, the outer ring (401) may be inflated, partially inflated, or fully deflated. The mouth of the patient is opened and their head positioned for insertion of the mask (100). The outer ring (401) is pushed into the orolaryngeal region. The smooth arcuate curves of the combined respiratory tube (205) and shield (201) positions the laryngeal mask (100) in alignment with the laryngeal opening. Upon proper positioning, as generally determined by a resistance to further forward motion, the outer ring (401) is inflated using the inflation device (405). When fully inflated, the outer ring (401) exerts sufficient pressure against the structures of the oropharynx to form a tight seal surrounding the laryngeal opening.

Positioned within the recessed cavity (511), the distal lumen (523) is axially aligned with the laryngeal opening, permitting positive lung ventilation to be performed, or allowing endo-tracheal tubes or related medical instruments inserted through the respiratory tube (205) to exit through the distal lumen (523) which is directly aligned for passage into the laryngeal opening. Removal of the laryngeal mask (100) is normally the reverse of the insertion procedure described above. As the device is generally relatively inexpensive to manufacture, once it has been removed the mask (100) will generally be discarded.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method of constructing a laryngeal mask airway; the method comprising providing a respiratory tube having a distal and a proximal end;
   blow-molding a shield, said shield formed as a single unitary piece comprising an inflatable outer ring formed of a single layer of material and a posterior base formed of at least a double layer of the same material, wherein the at least a double layer of the posterior base is formed by pushing together two opposing surfaces of the blow-molded shield;
   providing an inflation tube having a distal and a proximal end;
   assembling said airway by inserting said respiratory tube through said outer ring in such a manner that said respiratory tube intersects said outer ring so that there is no air transmission between said respiratory tube and said outer ring; and
   placing said distal end of said inflation tube within said outer ring.

2. The method of claim 1 wherein said posterior base is the base of a recessed cavity surrounded by said outer ring.

3. The method of claim 2 wherein said distal end of said respiratory tube extends into said recessed cavity.

4. The method of claim 1 wherein said double layer of said posterior base is more than twice as thick of said single layer of said inflatable outer ring.

5. The method of claim 1 wherein said airway is intended to be disposed of after a single use.

* * * * *